United States Patent [19]

Cannon

[11] Patent Number: 4,653,484
[45] Date of Patent: Mar. 31, 1987

[54] PENILE ERECTION AID

[76] Inventor: Lamar J. Cannon, 2155 Chestnut Hill Cir., Decatur, Ga. 30032

[21] Appl. No.: 800,801

[22] Filed: Nov. 22, 1985

[51] Int. Cl.$^4$ .............................................. A61F 5/41
[52] U.S. Cl. ...................................................... 128/79
[58] Field of Search .......................................... 128/79

[56] References Cited

U.S. PATENT DOCUMENTS

| | | | |
|---|---|---|---|
| 1,608,806 | 11/1926 | Nelson | 128/79 |
| 3,920,007 | 11/1975 | Line | 128/79 |
| 4,362,152 | 12/1982 | Gorokhovsky et al. | 128/79 |
| 4,429,689 | 2/1984 | Yanong | 128/79 |

FOREIGN PATENT DOCUMENTS

| | | | |
|---|---|---|---|
| 98024 | 9/1924 | Austria | 128/79 |
| 614549 | 5/1935 | Fed. Rep. of Germany | 128/79 |
| 519989 | 4/1940 | United Kingdom | 128/79 |
| 884357 | 12/1961 | United Kingdom | 128/79 |
| 154639 | 6/1961 | U.S.S.R. | 128/79 |

Primary Examiner—Gene Mancene
Assistant Examiner—Cary E. Stone
Attorney, Agent, or Firm—James B. Middleton

[57] ABSTRACT

A penile erection aid for assisting a flaccid or partially flaccid penis in penetration. The device includes a splint held to the under side of the penis, with an anchoring ring fixed to the splint and passing around the penis at the base of the extremity. The inner end of the splint is hinged to an anchoring ring that passes around the scrotum, the anchoring ring being held in place by straps. The straps include a body strap passing around the waist of the person, with one pair of straps connected to the anchoring ring, passing between the legs of the person, and connected to the body strap. Another pair of straps is connected to the front of the anchoring ring and extends up to connect to the body strap. The pair of straps connected to the front of the anchoring ring can be crossed to exert pressure at the base of the penis to assist in maintaining a partial natural erection. The anchoring ring is separable from the splint so the straps can be removed for cleaning or the like.

2 Claims, 4 Drawing Figures

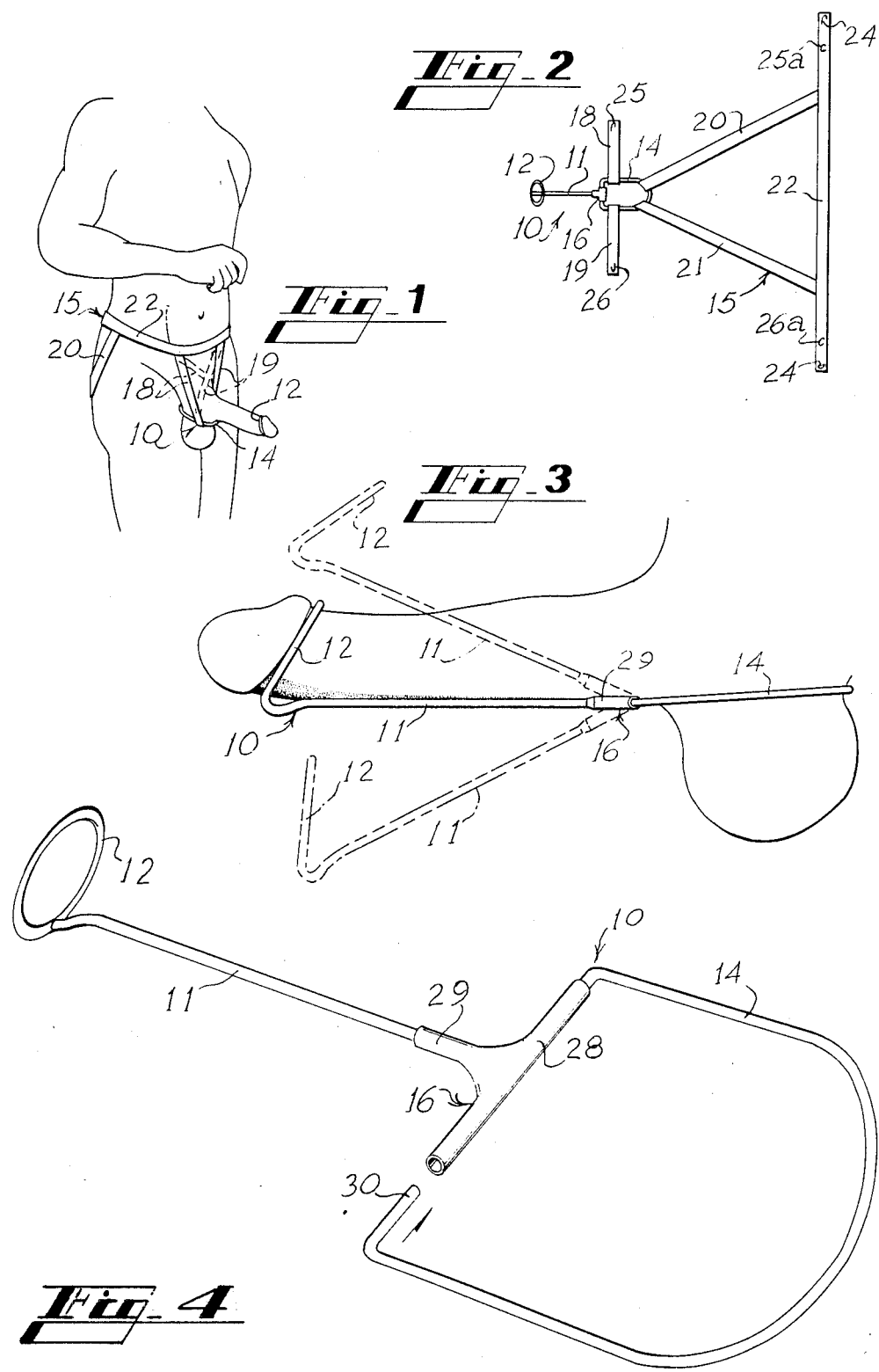

PENILE ERECTION AID

INFORMATION DISCLOSURE STATEMENT

The prior art includes many forms of devices and techniques for assisting a male in achieving sufficient erection for the male to engage successfully in sexual intercourse. These prior art devices include a large number of supports, or splints, to allow the male to achieve sufficient rigidity for penetration even when the male is partially disabled for any of numerous reasons. Such prior art splints include generally one or more substantially rigid members extending along the penis with one or more members substantially surrounding the penis so that the device is a typical splint lending its rigidity to an otherwise flaccid, or partially flaccid, member. The prior art apparatus provides a longitudinal splint, or support, but such devices generally fail to recognize the exceptional need for comfort, both for the male and for the female; rather, the prior art devices tend to render the entire procedure somewhat awkward, the splints being bulky and sometimes formed of numerous mechanical parts that may cause some trauma to one or both of the parties involved. Recent developments include an implant which requires major surgery, and may be quite hazardous to the patient.

SUMMARY OF THE INVENTION

This invention relates generally to medical accessories, and is more particularly concerned with a penile splint.

The present invention provides an erection aid including a single longitudinal splint member disposable along the lower surface of the penis, and a penis engaging member for engaging the penis at the base of the extremity, or glans penis. The present invention further includes anchoring means for holding the splint adjacent to the under side of the penis and preventing movement of the splint relative to the penis. In the preferred embodiment, the anchoring means comprises a loop extending around the scrotum, and strap means for holding the loop in place. The splint member is pivotal with respect to the anchoring member to provide a normal up and down motion while resisting lateral motion. The device of the present invention is preferably made of relatively small diameter material so that the apparatus can be installed on the penis prior to any degree of enlargement of the penis; thus, after some enlargement of the penis the structural members of the device may be partially surrounded by natural tissue to provide maximum comfort for the female.

BRIEF DESCRIPTION OF THE DRAWINGS

These and other features and advantages of the present invention will become apparent from consideration of the following specification when taken in conjunction with the accompanying drawings in which:

FIG. 1 is a perspective view showing an apparatus made in accordance with the present invention installed for use;

FIG. 2 is a top plan view showing the device of FIG. 1 with the strap means laid flat;

FIG. 3 is a side elevational view of the device shown in FIGS. 1 and 2, the strap means being omitted for clarity; and, FIG. 4 is an enlarged perspective view of the device shown in FIGS. 1–3 and illustrating the separability of the device.

DETAILED DESCRIPTION OF THE EMBODIMENT

Referring now more particularly to the drawings, and to that embodiment of the invention here presented by way of illustration, FIG. 1 illustrates an erection aid generally designated at 10 as it may be installed on the male. It will be seen that the splint 11 extends along the lower surface of the penis with a support ring 12 surrounding the penis at the base of the extremity.

At the inner end of the splint 11, there is an anchoring loop 14 surrounding the scrotum. Strap means generally designated at 15 are fixed to the anchoring ring 14. This structure will be discussed in more detail hereinafter.

Looking now at FIG. 2 in conjunction with FIG. 1, it will be seen that the anchoring ring 14 has a forward portion 16, the forward portion 16 comprising a tee having a generally straight portion. This tee 16 is for convenience of manufacture to provide the desired qualities, and will be discussed in more detail below.

It will also be seen in FIG. 2 that the strap means 15 includes a pair of forward straps 18 and 19 which are fixed to the anchoring ring 14 and extend outwardly therefrom. At the rear of the anchoring ring 14 there are two additional straps 20 and 21. These straps 20 and 21 are significantly longer than the straps 18 and 19, and extend rearwardly to be fixed to a body surrounding strap 22. The body surrounding strap 22 includes fastening means 24 at its extremities to allow the ends of the strap 22 to be fastened together. Any conventional fastening means may be used as the fastening means 24, including hooks and eyes, snaps and the like.

The straps 18 and 19 have fastening means 25 and 26 at their extremities, and these fastening means 25 and 26 are designed to mate with fastener parts 25a and 26a on the strap 22, inwardly of the fastening means 24.

With the above discussion in mind, it should now be understood that the device 10 will be placed on the penis, with the support ring 12 surrounding the penis and the anchoring ring 14 surrounding the scrotum. The straps 20 and 21 will be passed between the legs of the person, and the strap 22 will be passed around the person, approximately at the waist of the person. The strap 22 will be passed completely around the person and the fastening means 24 connected to each other. At this point, the straps 18 and 19 will be pulled up and the fastening means 25 and 26 will be engaged with the fastener parts 25a and 26a. This results in the arrangement as shown in FIG. 1, the front portion of the strap 22 being pulled down sufficiently to connect to the straps 18 and 19 while the straps 20 and 21 lie comfortably as they fall around the buttocks of the wearer.

As is shown in broken lines in FIG. 1, the straps 18 and 19 may be crossed if desired. The crossing will urge the anchoring ring 14 upwardly more firmly, and may assist in restricting blood flow to help maintain the natural erection.

Looking now at FIG. 3 of the drawings, the erection aid 10 is shown installed on a penis. The strap means 15 is omitted for clarity, but it will be understood that the anchoring ring 14 passes completely around the scrotum, and is held in that position by the strap means 15 as discussed above. Since the anchoring ring 14 is held up, and further urged upwardly, it will be readily seen that the entire device 10 will be prevented from moving longitudinally of the penis. Also, the splint 11 passes generally longtudinally of the penis and will be adjacent to the corpus spongiosum. The supporting ring 12 is fixed by welding or the like to the outer extremity of the splint 11, and the junction of the support ring 12 and the splint 11 will be carefully dressed to be completely smooth with no sharp corners or projections. The support ring 12 then completely surrounds the penis at the base of the extremity thereof.

It will be understood that the device of the present invention should be custom fitted to a given person so that the fit would be precise. When the device fits properly, it will be seen that the erection aid 10 can be installed as discussed above, with the penis lying along the splint 11 and extending at least somewhat through the support ring 12. If the penis is thereafter enlarged, the corpora cavernosa will be enlarged while the ring 12 of course remains of the same diameter so that the anchoring ring 12 is substantially confined within the tissue. Since the splint 11 is along the lower portion of the penis, the corpus spongiosum allows the splint 11 to be somewhat buried in the natural tissue so that the entire device 10 will not be particularly noticeable to the female. Additionally, the tee 16 provides for hinging of the erection aid 10 to allow normal up and down motion as shown by the broken line representations in FIG. 3.

Looking at FIG. 4 of the drawings, it will be seen that the tee 16 comprises a transverse barrel 28 and a perpendicular leg 29. The entire tee 16 will be smoothly finished so there will be no shrap edges or the like, and the arm 29 will be adapted to receive the splint 11 and to be fixed thereto. It is contemplated that the splint 11 will be received within the arm 29, and fixed in a permanent manner, a user buying one device that precisely fits that user so that the splint 11 will not need to be removed from the tee 16.

The anchoring ring 14 is here shown as comprising a D-shaped ring, the barrel 28 of the tee 16 constituting a hinge barrel with the legs such as the leg 30 of the anchoring ring 14 acting as hinge pintles. Also as shown in FIG. 4, it is preferred that the pintles 30 be selectively removable from the barrel 28 to allow the anchoring ring 14 to be separated from the tee 16 as desired. This simple construction allows the pivoting as discussed above, and also allows easy separation of the anchoring ring 14 from the tee 16 for installation and removal of the strap means 15.

Those skilled in the art will understand that many different materials of many different sizes may be utilized for the device of the present invention. It has been found, however, that approximately a 14 gauge wire (American Wire Gauge) of stainless steel works quite well, and is inoffensive to both the male and the female. The stainless steel wire for the anchoring ring 14 also allows sufficient elasticity for the pintles 30 to be normally urged into the barrel 28 of the tee 16, but to be removable at will.

Since the anchoring ring 14 is easily removable from the tee 16, it will be understood that the strap means 15 can be removed for crossing the straps 18 and 19 if desired, and also can be removed so the strap means 15 can be thoroughly washed. If the device 10 is made of stainless steel or the like, it will be understood that the entire device can be completely cleansed and sterilized using alcohol or other germicidal liquids. The strap means 15 may also be cleansed at the same time if desired, or the strap means can be removed and washed in a conventional manner, using additional germicidal materials if desired.

It will therefore be seen that the present invention provides an extremely simple device as an aid to a male who cannot achieve sufficient erection for penetration. The device is arranged to be held firmly in place to achieve maximum comfort by the male as well as by the female. While the device provides the necessary rigidity of the length of the penis, the device further allows normal flexibility with respect to the male's body for a more nearly natural relationship. While the strap means will efficiently hold the erection aid in place, the strap means can also be cuased to exert pressure at the base of the penis to assist the natural process.

It will of course be understood by those skilled in the art that the particular embodiment of the invention here presented is by way of illustration only, and is meant to be in no way restrictive; therefore, numerous changes and modifications may be made, and the full use of equivalents resorted to, without departing from the spirit or the scope of the invention as outlined in the appended claims.

I claim:

1. A penile erection aid of the type to be carried by a penis to assist a person in having sexual intercourse by aiding in penetration, said erection aid comprising a splint member disposable along the under side of said penis, a penis engaging member for holding the outer extending end of said splint against said penis, and anchoring means for holding the inner end of said splint in a generally fixed position with respect to said penis, said anchoring means including an anchoring ring surrounding the scrotum of said person, said anchoring ring having a front disposed at the front of said scrotum and a rear disposed at the rear of said scrotum, the arrangement being such that said scrotum maintains the position of said anchoring ring for preventing reciprocating motion of said splint with respect to said penis said penis engaging member including a support ring fixed to said splint and adapted to surround said penis at the base of the glans penis thereof, and including hinge means for hingedly connecting said splint to said anchoring ring, said hinge means including a hinge barrel disposable in the front of said scrotum with said splint extending perpendicularly therefrom, said anchoring ring defining pintles selectively receivable within said hinge barrel, said splint and said support ring being formed of wire, said erection aid being sized so that said wire becomes substantially embedded in penile tissue after enlargement of said penis.

2. A penile erection aid as claimed in claim 1, and further including strap means for holding said anchoring ring in position around said scrotum, said strap means including a first pair of straps carried by said rear of said anchoring ring, said first pair of straps passing between the legs of said person adjacent to the prostate gland of the said person, said strap means further including a second pair of straps carried by said front of said anchoring ring, a body surrounding strap for passing completely around the body of said person, said first pair of straps being fixed to said body surrounding strap, and fastening means for selectively fixing said second pair of straps to said body surrounding strap, said first pair of straps and said second pair of straps being elastic and extending upwardly for connection to said body surrounding strap so that said anchoring ring is urged upwardly for secure positioning with respect to said scrotum.

* * * * *